United States Patent [19]

Tan et al.

[11] Patent Number: 4,825,879

[45] Date of Patent: May 2, 1989

[54] PULSE OXIMETER SENSOR

[75] Inventors: J. Kie S. Tan, Tampa; Jeffrey A. Baker, Lutz; Daniel A. Jones, Tampa, all of Fla.

[73] Assignee: Critkon, Inc., Tampa, Fla.

[21] Appl. No.: 107,085

[22] Filed: Oct. 8, 1987

[51] Int. Cl.[4] ............................................. A61B 5/00
[52] U.S. Cl. ................................. 128/633; 128/636; 128/637; 128/672; 128/677
[58] Field of Search ............ 128/632, 633, 637, 644, 128/664, 665, 666, 667, 672, 677, 686, 346, 687, 689

[56] References Cited

U.S. PATENT DOCUMENTS

| | | | |
|---|---|---|---|
| 3,229,685 | 1/1966 | Ringkamp et al. | 128/667 |
| 3,482,565 | 12/1969 | Gowen | 128/667 |
| 4,406,289 | 9/1983 | Wesseling et al. | 128/672 X |
| 4,539,997 | 10/1985 | Wesseling et al. | 128/677 X |
| 4,545,387 | 10/1985 | Balique | 128/668 X |
| 4,685,464 | 8/1987 | Goldberger et al. | 128/633 |
| 4,714,080 | 12/1987 | Edgar, Jr. et al. | 128/666 X |
| 4,726,382 | 2/1988 | Boehmer et al. | 128/686 X |

Primary Examiner—Lloyd L. King
Attorney, Agent, or Firm—W. Brinton Yorks, Jr.

[57] ABSTRACT

A pulse oximeter sensor is provided in which the wrap which encloses and secures the light source and detector to the body includes a sheet of metallized material. The metallized material reflects body heat back to the body and provides opacity to interfering ambient light. The wrap may be formed in a "T" shape, with the light sensor and detector aligned with the stem of the "T", or in a disposable elongated configuration with the light sensor and detector longitudinally aligned with the wrap. The wrap is secured during use through either adhesive means or by the use of hook and loop fabric patches.

19 Claims, 4 Drawing Sheets

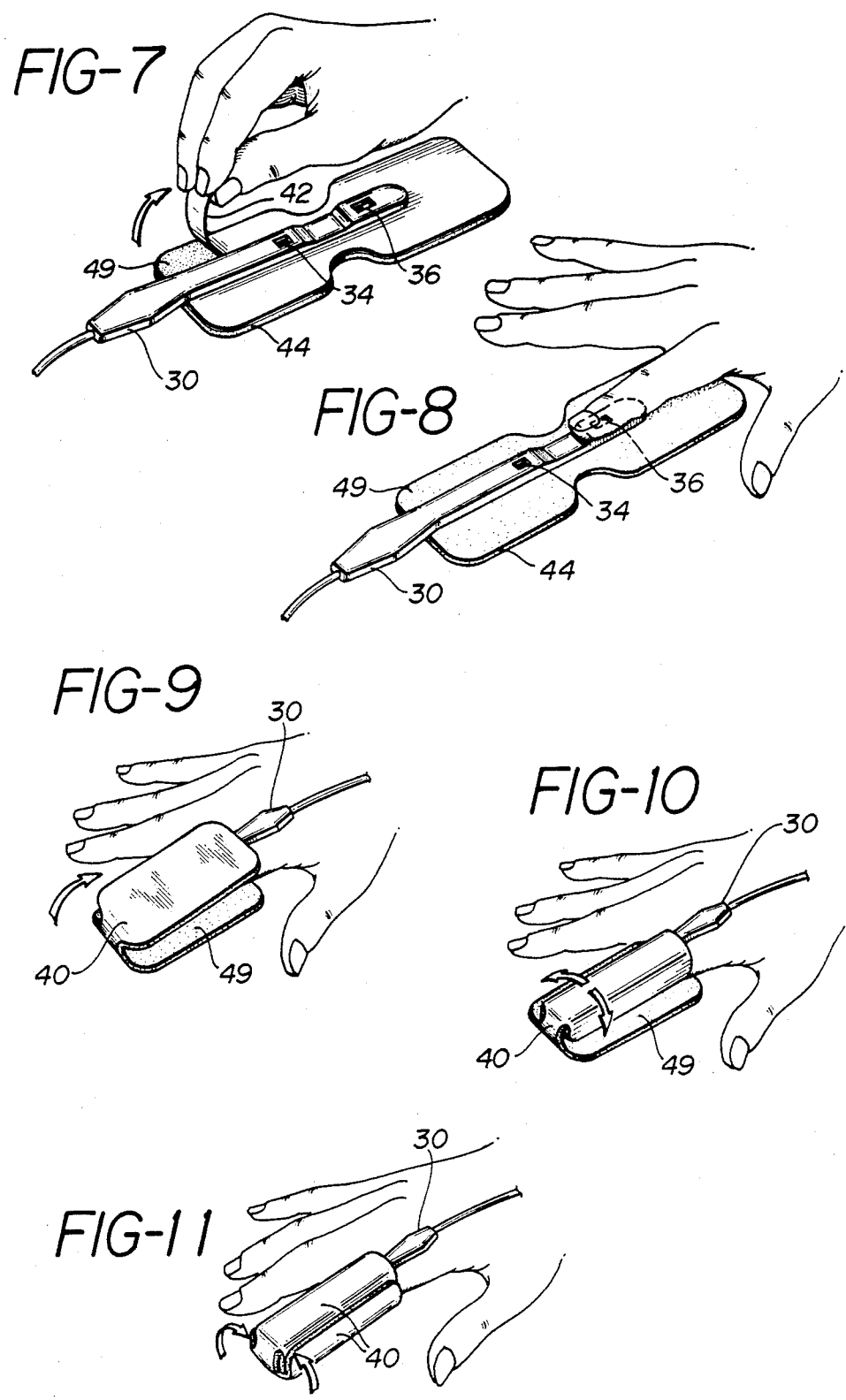

PULSE OXIMETER SENSOR

This invention relates to medical sensors for detecting physiological functions and, in particular, to an optical sensor for detecting vascular flow in a pulse oximetry system.

Pulse oximetry is a non-invasive medical technique useful for measuring certain vascular conditions. In practice of the technique, light is passed through a portion of a patient's body which contains arterial blood flow. An optical sensor is used to detect the light which has passed through the body, and variations in the detected light at various wavelengths are then used to determine arterial oxygen saturation and/or pulse rates. Oxygen saturation may be calculated using some form of the classical absorption equation known as Beier's Law.

Accurate measurements of these physiological functions are predicated upon optical sensing in the presence of arterial blood flow. Conveniently a finger may serve this purpose, which allows easy access to a body part through which light will readily pass. Local vascular flow in a finger is dependent upon several factors which affect the supply of blood. Blood flow may be affected by centrally mediated vasoconstriction, which must be alleviated by managing the perceived central causes. Peripheral construction, however, can be induced by local causes. One such cause of local vasoconstriction is low ambient temperature, which is a particular problem for body extremities such as the finger. Low temperature induced vasoconstriction and the resultant decrease in blood supply can strongly affect the sensor's ability to detect the desired signal.

Conventional attempts to alleviate the problem of low temperture vasoconstriction include the use of an integral heater to the sensor and periodic massaging. Heaters must be well regulated to avoid overheating, increase the complexity of the sensor, and can be costly. Periodic massaging can be effective, but usually requires removal of the sensor while the sensor locality is massaged. After some massaging of the locality to stimulate blood flow to it, the sensor is reapplied and measurement resumed. It would be desirable to employ a less complex, passive means for retaining body heat which does not interrupt the measurement process.

In sensors which detect light transmitted through a portion of the body, ambient light sources may interfere with the signal being observed. Because skin tissue is translucent, outside light is easily scattered and transmitted within the tissue toward the optical detector of the sensor. It is desirable to shield the detector from ambient light for a distance of approximately one-half inch around the detector area. A combination of the use of an opaque material and an effective sensor design will contribute significantly to the prevention of ambient light interference.

In accordance with the principles of the present invention, a pulse oximeter sensor is provided which reduces signal loss due to thermal vasoconstriction and ambient light interference. The sensor includes a light emitting diode (LED) light source and a photodiode for detecting light from the source. The LED and the photodiode are spaced apart on the body-facing side of a sensor wrap which secures the LED and photodiode on the body. The sensor wrap comprises a metallized film which is laminated to a backing material. The metallized layer is thermally reflective so as to reflect body heat back to the body, and is opaque so as to shield the photodiode from ambient light. The metallized layer may also be grounded to shield the sensor's electrical components from electromagnetic interference. The backing material may comprise insulating material such as foam to provide additional comfort and compliance of the wrap. Means are provided for securing the sensor wrap around a body part such as a finger.

IN THE DRAWINGS

FIG. 7–11 illustrate use of the sensor of FIGS. 2a–2c.

Figure 1A:
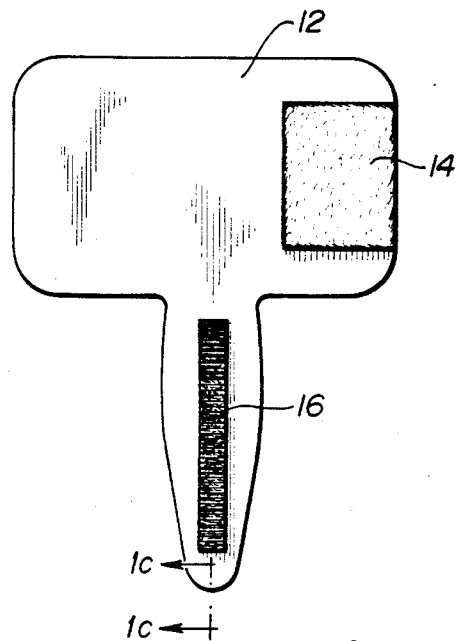
FIGS. 1a–1c illustrate plan and cross-sectional views of a sensor constructed in accordance with the principles of the present invention.
Figure 1B:
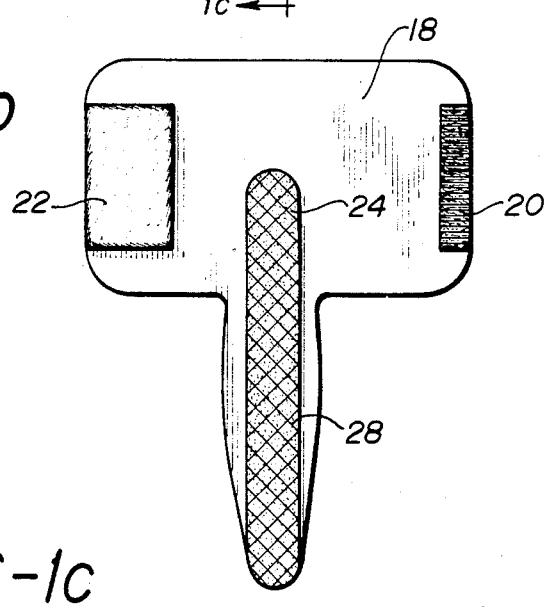
Figure 1C:
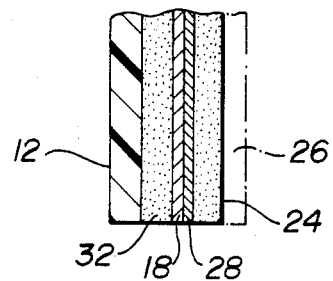

Referring to FIGS. 1a–1c, an oximeter sensor wrap constructed in accordance with the principles of the present invention is shown. FIG. 1a is a plan view of the outside of a finger wrap, with the outer surface 12 comprising a sheet of soft, compliant polyvinylchloride (PVC) film material. The wrap has a length (from top to bottom in the drawing) of approximately 4½ inches, and a width (across the top) which varies from 3 to 3.9 inches, depending upon the finger size for which the wrap is designed. On the right inner surface of the wrap is a means 14 for securing the wrap about the finger of a patient. This means may be an area of contact adhesive, but in the illustrated embodiment of FIG. 1a the securing means comprises a patch of tricot loop material which is adhesively laminated to the PVC sheet. A suitable tricot loop material is type SJ3491, available from Minnesota Mining and Manufacturing Company of St. Paul, Minn., which is affixed with 3M type Y9485 adhesive laminate.

A second securing means 16 is located along the center of the lower extension of the wrap. This securing means 16 may also be a contact adhesive, but in the illustrated embodiment the means 16 comprises a strip of 3M Scotchmate hook material type SJ 3526 which is adhesively laminated to the wrap. The hook material is designed to mate with the tricot loop material in a secure but releasable engagement as discussed below in conjunction with FIGS. 3–6. The hook and loop securing means is preferred over adhesive securing means because it permits repeated use of the wrap.

The inner, or finger facing side of the wrap is shown in FIG. 1b. The inner surface 18 of the wrap comprises a sheet of metallized polyester film material, which is described more fully below. Securing means 20 and 22 are located on the inner surface 18 and may comprise contact adhesive. Preferably, the means 20 comprises a patch of the tricot loop material described above, and the means 22 comprises a patch of the hook material. Running along the stem of the T-shaped wrap and extending upward to approximately the center of the top of the "T" is an area 24 of the type Y9485 adhesive. A cross-hatched ink pattern 28 is printed beneath the adhesive and is visible through the adhesive. This pattern indicates to the user the area in which the LED strip of the sensor is to be placed, as discussed below. To protect the adhesive area 24 from unintended adhesion and contamination prior to use, the adhesive area 24 is covered with a release strip 26 of silicone coated kraft paper.

Referring to FIG. 1c, a cross-sectional view of the layers comprising the wrap of FIGS. 1a and 1b is shown. The PVC layer 12 which comprises the outer surface of the wrap has a thickness of approximately 13 mils, and the PVC film is reinforced with polyester fibers. This compliant layer 12 is fairly opaque to shade the photodiode in the LED strip from ambient light. The release strip 26 is shown covering the adhesive area 24, which overlies the cross-hatched ink pattern 28. In accordance with the principles of the present invention, the inner surface of the wrap comprises a layer 18 of 1 mil aluminum metallized polyester film. The metallized film is available from Tapemark Co. of W. St. Paul, Minn. The resistance of the metallization corresponds directly to the thickness of the metallization on the film and in the illustrated embodiment the metallization has a resistance of less than two ohms per square. This metallization provides the film with an opacity of better than 95%. The metallized surface of the film has a soft matte finish which is non-glaring. The metallized film layer 18 is laminated too the PVC layer 12 with the type Y9485 adhesive as shown by adhesive layer 32. The metallized film provides the sensor with the desired degree of protection from ambient light interference, as well as high thermal protection for the finger. It has been found that approximately 70–80% of body heat loss is through radiation. The metallized inner surface of the wrap is effective for reflecting a substantial portion of this radiated heat back to the finger, thereby aiding in the reduction of thermal vasoconstriction. The combined opacity and reflective properties of the metallized layer help maintain the conditions needed for good signal reception by the sensor.

If desired, the metallized layer may be electrically grounded to a connection from the LED strip to help shield the electronic components in the LED strip from electromagnetic interference.

Figure 3:
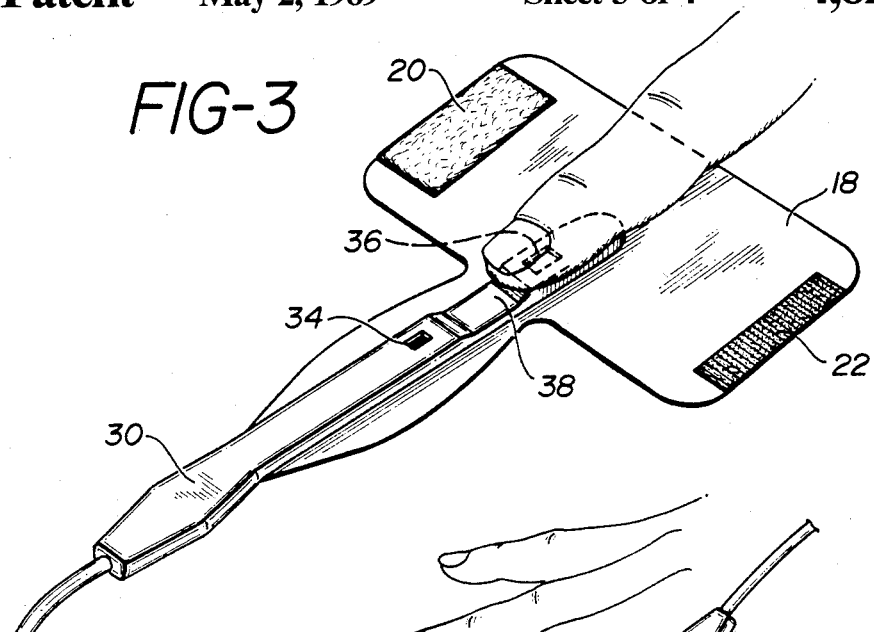
FIGS. 3–6 illustrate use of the sensor of FIGS. 1a–1c.

In use, the release strip 26 is peeled away to uncover the adhesive area 24 for the LED strip. The LED strip 30 is then affixed to the adhesive area as shown in FIG. 3. The LED strip 30 is made of a rubber-like material of a medical grade, such as silicone rubber, polyurethane, or PVC. The upper surface of the strip 30 has a window for LED's 34 and a second window for a photodiode 36. Between the two is a shallow depression 38 which allows the LED strip 30 to be folded over the fingertip. Wiring inside the strip 30 connects the LEDs and photodiode to a cable at the end of the strip, either through discrete wires or flexible printed wiring. The rubber-like LED strip may be molded around the electronic components, or may be formed in two halves which are then laminated together. The rubber-like strip is waterproof so that the strip may be washed between uses.

Figure 4:
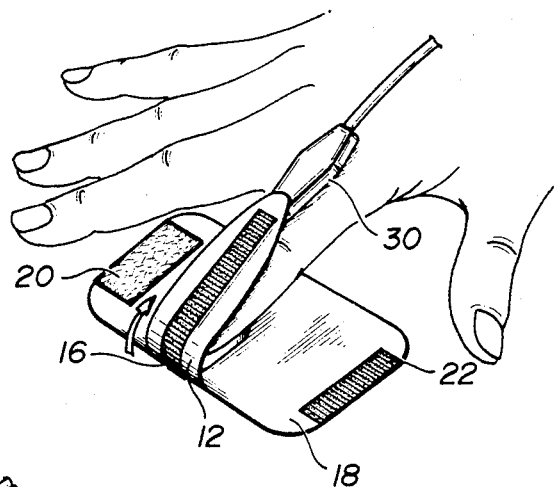
Figure 5:
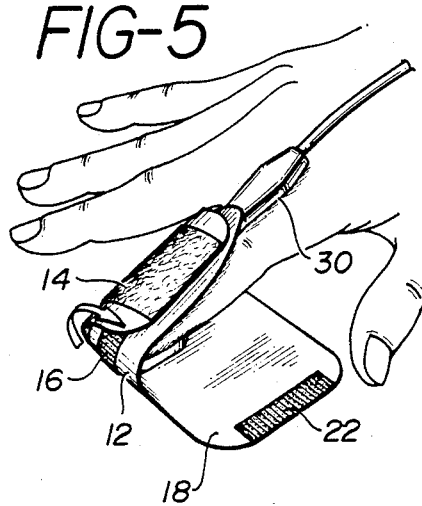
Figure 6:
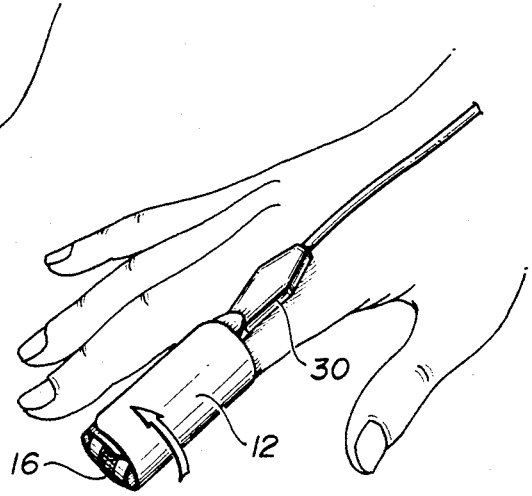

After the fingertip is placed on the photodiode 36 as shown in FIG. 3, the stem of the T-shaped wrap with the attached LED strip is folded over the top of the finger as shown in FIG. 4. Then the left side of the wrap is folded over the stem of the "T" so that the tricot loop patch 20 is secured to the hook material 16. This step is shown in FIG. 5. Finally, the right side of the wrap is folded over the finger so that the patch 22 of hook material fastens to the tricot loop patch 14, as shown in FIG. 6. The sensor is thus securedly wrapped around the finger, with the finger surrounded by the metallized film layer 18.

After the measurement process is finished, the sensor is unwrapped and the LED strip may be removed from the adhesive area 24 for washing and reuse in another procedure. The hook and loop securing means permit the sensor to be easily unwrapped and resecured if it is desirable to do so during a measurement procedure.

Figure 2A:
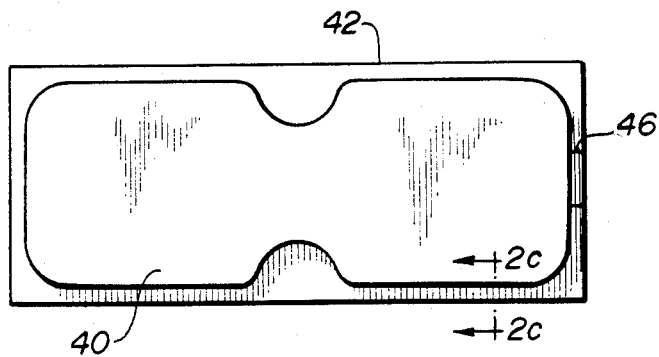
FIGS. 2a–2c illustrate plan and cross-sectional views of a second embodiment of the present invention.
Figure 2B:
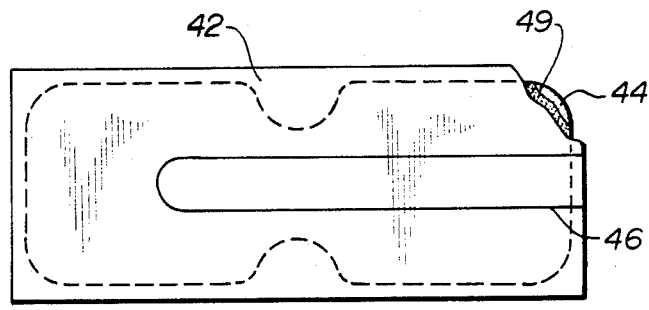
Figure 2C:
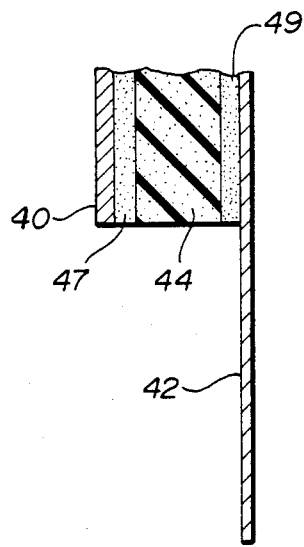

Referring to FIGS. 2a–2c, a disposable wrap for an oximeter sensor is shown. FIG. 2a shows the outer surface of the wrap, which comprises a layer 40 of 1 mil metallized polyester film. The wrap is approximately 5 inches long and 2 inches wide, and is narrowed in the central region where the wrap folds around the fingertip. Located on the back, or finger-facing side of the wrap is a sheet of release paper 42, shown in the back view of FIG. 2b. The back of the wrap comprises a sheet 44 of medical grade foam, which is coated with Semex type TT4025 adhesive. The release paper 42 covers the adhesive surface prior to use. A central longitudinal region 46 of the release paper is perforated, allowing this region of the wrap to be uncovered first. The LED strip 30 is then affixed to this initially uncovered adhesive region. Once the LED strip is attached to the wrap, the remaining release paper is peeled away to enable the sensor to be secured to a finger.

A cross-sectional view of the wrap of FIGS. 2a and 2b is shown in FIG. 2c. The release paper 42 is seen overlying the adhesive coating 49 on the foam layer 44. The preferred foam layer is approximately 30 mils thick, and is available from Semex Medical Company of Malvern, Pa. as type KM-1422. The foam layer 44 is conformable to the finger of the patient and provides a degree of comfort during use. The matte finished aluminum metallized polyester film layer 40 is laminated to the foam layer by an adhesive 47.

In the FIGS. 2a–2c embodiment, the use of the metallized film as the outer layer provides the same opacity and heat reflective properties as the embodiment of FIGS. 1a–1c. If desired, the foam and metallized film layers could be exchanged so that the metallized film layers directly opposes the finger and the foam is on the outside.

Use of the wrap of FIGS. 2a–2c is depicted in FIGS. 7–11. In FIG. 7 the LED strip 30 is shown affixed to the central longitudinal region of the wrap after the center strip 46 of the release paper has been removed. The remaining release paper is then peeled away as shown in FIG. 7. Next, the fingertip is placed over the photodiode 36, as shown in FIG. 8. The wrap and LED strip are folded over the fingertip as shown in FIG. 9. The areas of the wrap on either side of the LED strip are folded down about the finger as shown in FIG. 10. Finally, the lower sides of the wrap are folded up over the outer surface of the wrap, as shown in FIG. 11, so that the adhesive coating 49 seals the overwrapped sides together. Removal of the sensor will generally impair the adhesive or tear the foam, so the wrap is then removed from the LED strip and disposed of when the measurement procedure is complete.

What is claimed is:

1. In apparatus for sensing light absorption through transillumination of blood perfused flesh by a light source and reception of light by a light sensor; a wrap for securing said light source and sensor in optical contact with a patent comprising: an outer, flexible layer of polymeric material; and an innermost, body facing layer comprising a compliant sheet of metallized material which is capable of reflecting body heat and is highly opaque, and means for securing said sheet to the body of a patient.

2. The apparatus of claim 1, further comprising means for securing said light source and said light sensor to said wrap.

3. The apparatus of claim 1, wherein said outer layer comprises a layer of fabric.

4. The apparatus of claim 3, wherein said outer fabric layer comprises a layer of polyvinylchloride laminated to said sheet of metallized material.

5. The apparatus of claim 4, wherein said securing means comprises mating pieces of hook material and loop material.

6. In apparatus for sensing light absorption through transillumination of blood perfused flesh by a light source and reception of light by a light sensor; a wrap for securing said light source and sensor in optical contact with a patient comprising: a generally rectangular inner sheet of compliant material having an adhesive coated, body facing side, longitudinal edges extending along each side of said sheet in the longitudinal dimension, and a central region intermediate the longitudinal ends of said sheet which is intended to engage the tip of a finger; and an outer sheet of metallized material, wherein, when said wrap engages a finger tip at said central region and said wrap is folded over opposing sides of said finger, the opposing, adhesive-coated longitudinal edges of said wrap may be sealed together.

7. The apparatus of claim 6, further comprising a removable strip containing a light source and a light sensor, and intended for longitudinal attachment to said inner sheet with said light source and said light sensor positioned on longitudinally opposite sides of said central region.

8. The apparatus of claim 6, wherein said compliant material comprises a foam sheet which is laminated to said metallized material.

9. The apparatus of claim 7, wherein said adhesive coating comprises pressure sensitive adhesive.

10. The apparatus of claim 9, wherein said pressure sensitive adhesive is covered with release paper prior to use.

11. The apparatus of claim 1, wherein said sheet of metallized material comprises aluminum metallized polyester film.

12. In apparatus for sensing light absorption through transillumination of blood perfused flesh by a light source and reception of light from said source by a light sensor; a wrap of securing said light source and sensor in optical contact with a finger, comprising a generally T-shaped sheet of material, the stem of the "T" including means for affixing said light source and sensor to said wrap, and the top of the "T" including means, laterally disposed therein, for securing the top of the "T" in a folded condition around a finger, wherein electrical connections to said light source and light sensor extend in a direction generally parallel to the longitudinal axis of a finger when the wrap is secured to the finger.

13. The apparatus of claim 12 further comprising means, located on the stem of the "T", for securing the stem of the "T" in a folded condition to the top of the "T".

14. The apparatus of claim 13, wherein said affixing means comprises an adhesive area.

15. The apparatus of claim 14, wherein said securing means comprise mating pieces of hook material and loop material.

16. In apparatus for sensing light absorption through transillumination of blood perfused flesh by a light source and reception of light from said source by a light sensor, a wrap for securing said light source and sensor in optical contact with a finger comprising an elongated sheet of material having a longitudinal dimension and a lateral dimension across which said wrap is folded during use, the finger contacting surface of said sheet being coated with an adhesive; and means for protecting said adhesive from unintended adhesion prior to use; said finger contacting surface including a longitudinal region for attaching said light source and sensor and their electrical connections in alignment with the longitudinal dimension of said sheet of material.

17. The apparatus of claim 16, wherein said protecting means includes means for uncovering said longitudinal region prior to uncovering the remainder of said finger contacting surface.

18. The apparatus of claim 17, wherein said protecting means comprises a sheet of perforated release paper, perforated about the area of said longitudinal region.

19. The apparatus of claim 16, wherein the lateral dimension of said sheet of material is narrowed in the region across which said wrap is to be folded during use.

* * * * *